(12) United States Patent
Thomas, III et al.

(10) Patent No.: US 9,427,210 B2
(45) Date of Patent: Aug. 30, 2016

(54) IMAGING DEVICES WITH AN ARRAY OF TRANSDUCERS AND METHODS OF MANUFACTURE AND USE

(71) Applicant: Boston Scientific SciMed, Inc., Maple Grove, MN (US)

(72) Inventors: Lewis Jones Thomas, III, Palo Alto, CA (US); Wenguang Li, Santa Clara, CA (US); Anming He Cai, San Jose, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 153 days.

(21) Appl. No.: 14/192,205

(22) Filed: Feb. 27, 2014

(65) Prior Publication Data

US 2014/0243679 A1    Aug. 28, 2014

Related U.S. Application Data

(60) Provisional application No. 61/770,733, filed on Feb. 28, 2013.

(51) Int. Cl.
*A61B 8/00*    (2006.01)
*A61B 8/12*    (2006.01)
(Continued)

(52) U.S. Cl.
CPC ............... *A61B 8/4483* (2013.01); *A61B 8/12* (2013.01); *A61B 8/445* (2013.01); *G01S 15/8915* (2013.01); *G01S 15/8927* (2013.01); *G01S 15/8997* (2013.01); *G01S 7/52077* (2013.01); *G01S 15/8956* (2013.01)

(58) Field of Classification Search
CPC ...... A61B 8/4483; A61B 8/12; A61B 8/445; G01S 15/8927; G01S 15/8997; G01S 15/8915; G01S 7/52077; G01S 15/8956

USPC .................................................. 600/437–469
See application file for complete search history.

(56) References Cited

U.S. PATENT DOCUMENTS

| 6,048,315 | A  | 4/2000 | Chiao et al. |
| 6,945,938 | B2 | 9/2005 | Grunwald |
| 7,246,959 | B2 | 7/2007 | Nakatani |

(Continued)

OTHER PUBLICATIONS

Partial International Search Report for PCT/US2014/019050 mailed Jul. 16, 2014.

(Continued)

*Primary Examiner* — Sanjay Cattungal
(74) *Attorney, Agent, or Firm* — Lowe Graham Jones PLLC; Bruce E. Black

(57) ABSTRACT

A medical imaging assembly includes an elongated catheter having a connector at the proximal end; an array of transducers on the distal end of the catheter; conductors electrically coupled to the array of transducers and in electrical communication with the connector of the catheter; and a control unit coupleable to the catheter to send and receive electrical signals between the control unit and the array of transducers through the connector of the catheter. The control unit has a processor to execute instructions including 1) selecting a first subset of M transmitting transducers and a second subset of N receiving transducers from the array of transducers, where N>M; and 2) for each of at least N transmit/receive cycles, a) directing the first subset of M transmitting transducers to transmit an acoustic signal; and b) directing the second subset of N receiving transducers to receive corresponding echo signals.

19 Claims, 8 Drawing Sheets

(51) Int. Cl.
  *G01S 15/89* (2006.01)
  *G01S 7/52* (2006.01)

(56) References Cited

U.S. PATENT DOCUMENTS

| | | |
|---|---|---|
| 7,306,561 B2 | 12/2007 | Sathyanarayana |
| 2003/0229286 A1 | 12/2003 | Lenker |
| 2006/0100522 A1 | 5/2006 | Yuan et al. |
| 2006/0106320 A1 | 5/2006 | Barbato |
| 2006/0173350 A1 | 8/2006 | Yuan et al. |
| 2006/0253028 A1 | 11/2006 | Lam et al. |
| 2007/0016054 A1 | 1/2007 | Cao et al. |
| 2007/0038111 A1 | 2/2007 | Rehrig et al. |
| 2007/0167752 A1* | 7/2007 | Proulx ............ G01S 7/52095 600/437 |
| 2007/0242567 A1 | 10/2007 | Daft et al. |
| 2009/0079299 A1 | 3/2009 | Bradley et al. |

OTHER PUBLICATIONS

International Search Report and Written Opinion for PCT/US2014/019050 mailed Nov. 4, 2014.

* cited by examiner

IMAGING DEVICES WITH AN ARRAY OF TRANSDUCERS AND METHODS OF MANUFACTURE AND USE

CROSS-REFERENCE TO RELATED APPLICATIONS

This application claims the benefit under 35 U.S.C. §119 (e) of U.S. Provisional Patent Application Ser. No. 61/770,733 filed Feb. 28, 2013, which is incorporated herein by reference.

TECHNICAL FIELD

The present invention is directed to the area of imaging systems that are insertable into a patient and methods of making and using the imaging systems. The present invention is also directed to catheters and systems having an array of transducers, as well as methods of making and using the catheters and systems including methods of operation with simultaneous reception of echo signals at multiple transducers.

BACKGROUND

Ultrasound devices insertable into patients have proven diagnostic capabilities for a variety of diseases and disorders. For example, intravascular ultrasound ("IVUS") imaging systems have been used as an imaging modality for diagnosing blocked blood vessels and providing information to aid medical practitioners in selecting and placing stents and other devices to restore or increase blood flow. IVUS imaging systems have been used to diagnose atheromatous plaque build-up at particular locations within blood vessels. IVUS imaging systems can be used to determine the existence of an intravascular obstruction or stenosis, as well as the nature and degree of the obstruction or stenosis. IVUS imaging systems can be used to visualize segments of a vascular system that may be difficult to visualize using other intravascular imaging techniques, such as angiography, due to, for example, movement (e.g., a beating heart) or obstruction by one or more structures (e.g., one or more blood vessels not desired to be imaged). IVUS imaging systems can be used to monitor or assess ongoing intravascular treatments, such as angiography and stent placement in real (or almost real) time. Moreover, IVUS imaging systems can be used to monitor one or more heart chambers.

IVUS imaging systems have been developed to provide a diagnostic tool for visualizing a variety of diseases or disorders. An IVUS imaging system can include a control module (with a pulse generator, an image processor, and a monitor), a catheter, and one or more transducers disposed in the catheter. The transducer-containing catheter can be positioned in a lumen or cavity within, or in proximity to, a region to be imaged, such as a blood vessel wall or patient tissue in proximity to a blood vessel wall. The pulse generator in the control module generates electrical pulses that are delivered to the one or more transducers and transformed to acoustic pulses that are transmitted through patient tissue. Reflected pulses of the transmitted acoustic pulses are absorbed by the one or more transducers and transformed to electric pulses. The transformed electric pulses are delivered to the image processor and converted to an image displayable on the monitor. In many conventional IVUS imaging systems, the transducers in the catheter rotate in order to obtain a full 360° image. The transducers are disposed on a driveshaft that is coupled to a motor to which the catheter is attached. Such arrangements necessarily require a minimum catheter diameter to ensure free and consistent rotation of the transducers.

BRIEF SUMMARY

One embodiment is a medical imaging assembly that includes an elongated catheter having a proximal end, a distal end, a longitudinal axis, and a connector disposed at the proximal end; an array of transducers arranged on the distal end of the catheter, each transducer configured and arranged for transforming applied electrical signals to acoustic signals, transmitting the acoustic signals, receiving corresponding echo signals, and transforming the received echo signals to electrical signals; a plurality of conductors electrically coupled to the array of transducers and in electrical communication with the connector of the catheter; and a control unit coupleable to the catheter and configured and arranged to send and receive electrical signals between the control unit and the array of transducers through the connector of the catheter. The control unit has a processor configured and arranged to execute instructions including 1) selecting a first subset of M transmitting transducers from the array of transducers and selecting a second subset of N receiving transducers from the array of transducers, wherein M and N are each integers equal to or less than a total number of transducers in the array of transducers and N>M; and 2) for each of at least N transmit/receive cycles, a) directing the first subset of M transmitting transducers to transmit an acoustic signal; and b) directing the second subset of N receiving transducers to receive corresponding echo signals arising in response to the transmitted acoustic signal.

Another embodiment is a non-transitory computer-readable medium having processor-executable instructions for processing signals from an array of transducers. The processor-executable instructions when installed onto a device enable the device to perform actions including 1) selecting a first subset of M transmitting transducers from the array of transducers and selecting a second subset of N receiving transducers from the array of transducers, where M and N are each integers equal to or less than a total number of transducers in the array of transducers and N>M; and 2) for each of at least N transmit/receive cycles, a) directing the first subset of M transmitting transducers to transmit an acoustic signal; b) directing the second subset of N receiving transducers to receive corresponding echo signals arising in response to the transmitted acoustic signal; and c) combining the echo signals from the transducers of the second subset to give a combined signal. The combined signal C(h,t) for the h-th transmit/receive cycle over time, t, has the form $$C(h, t) = \sum_{e=1}^{N} H_{he} R(e, t),$$

where R(e,t) is the echo signal from the e-th transducer of the second subset for the h-th transmit/receive cycle, and $H_{he}$ is a non-zero coefficient. The coefficients $H_{he}$ are selected so that a composite signals of the received echo signals from N of the transmit/receive cycles for any one of the transducers of the subset can be recovered by combining N of the combined signals by selective addition and subtraction of the N combined signals.

Yet another embodiment is a medical imaging assembly including an elongated catheter having a proximal end, a distal end, a longitudinal axis, and a connector disposed at the proximal end; an array of transducers arranged on the distal end of the catheter, each transducer configured and arranged for transforming applied electrical signals to acoustic signals, transmitting the acoustic signals, receiving corresponding echo signals, and transforming the received echo signals to electrical signals; a plurality of conductors electrically coupled to the array of transducers and in electrical communication with the connector of the catheter; and a control unit coupleable to the catheter and configured and arranged to send and receive electrical signals between the control unit and the array of transducers through the connector of the catheter. The medical imaging assembly is configured and arranged to operate at a transducer center frequency of at least 30 MHz.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of imaging systems that are insertable into a patient and methods of making and using the imaging systems. The present invention is also directed to catheters and systems having an array of transducers, as well as methods of making and using the catheters and systems including methods of operation with simultaneous reception of echo signals at multiple transducers.

Suitable intravascular ultrasound ("IVUS") systems and devices include, but are not limited to, an array of transducers disposed on a distal end of a catheter configured and arranged for percutaneous insertion into a patient. Examples of IVUS imaging systems with catheters are found in, for example, U.S. Pat. Nos. 7,246,959; 7,306,561; and 6,945,938; as well as U.S. Patent Application Publication Nos. 2006/0100522; 2006/0106320; 2006/0173350; 2006/0253028; 2007/0016054; and 2007/0038111; all of which are incorporated herein by reference.

Figure 1:
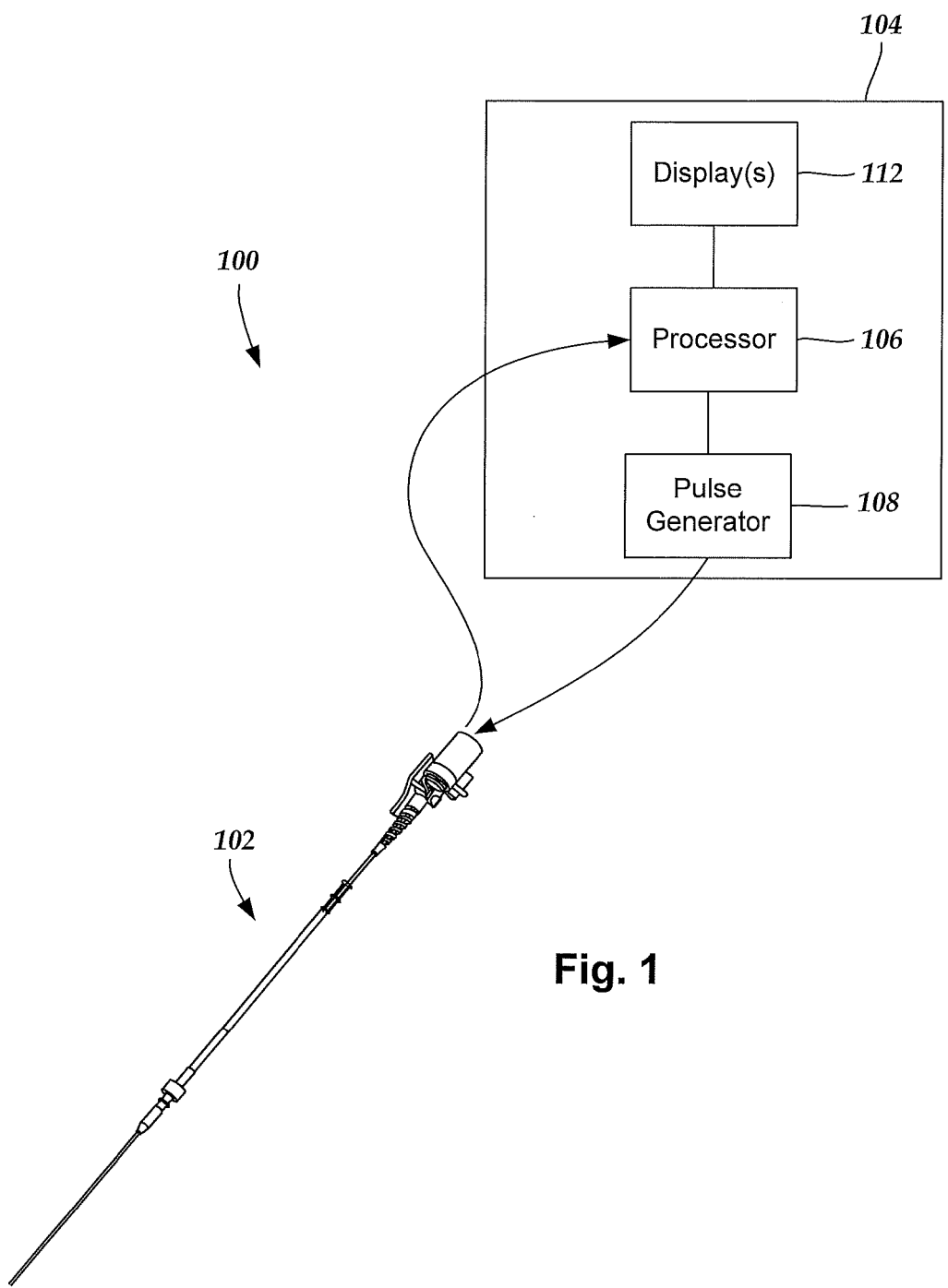
FIG. 1 is a schematic view of one embodiment of an ultrasound imaging system suitable for insertion into a patient, the ultrasound imaging system including a catheter and a control module, according to the invention.

FIG. 1 illustrates schematically one embodiment of an IVUS imaging system 100. The IVUS imaging system 100 includes a catheter 102 that is coupleable to a control module 104. The control module 104 may include, for example, a processor 106, a pulse generator 108, and one or more displays 112. In at least some embodiments, the pulse generator 108 forms electric pulses that may be input to an array of transducers (312 in FIG. 3) disposed in the catheter 102. Optionally, the control unit may include a drive unit to pullback the catheter or a portion of the catheter during a scanning procedure.

In at least some embodiments, electric signals transmitted from the transducers (312 in FIG. 3) may be input to the processor 106 for processing. In at least some embodiments, the processed electric signals from the transducers (312 in FIG. 3) can be displayed as one or more images on the one or more displays 112. For example, a scan converter can be used to map scan line samples (e.g., radial scan line samples, or the like) to a two-dimensional Cartesian grid to display the one or more images on the one or more displays 112. The processor 106 may also be used to implement the processes illustrated by the flowcharts in FIGS. 5 and 8 or any portion of those processes.

In at least some embodiments, the processor 106 may also be used to control the functioning of one or more of the other components of the control module 104. For example, the processor 106 may be used to control at least one of the frequency or duration of the electrical pulses transmitted from the pulse generator 108, the velocity or length of the pullback of the catheter by the drive unit, or one or more properties of one or more images formed on the one or more displays 112.

Figure 2:
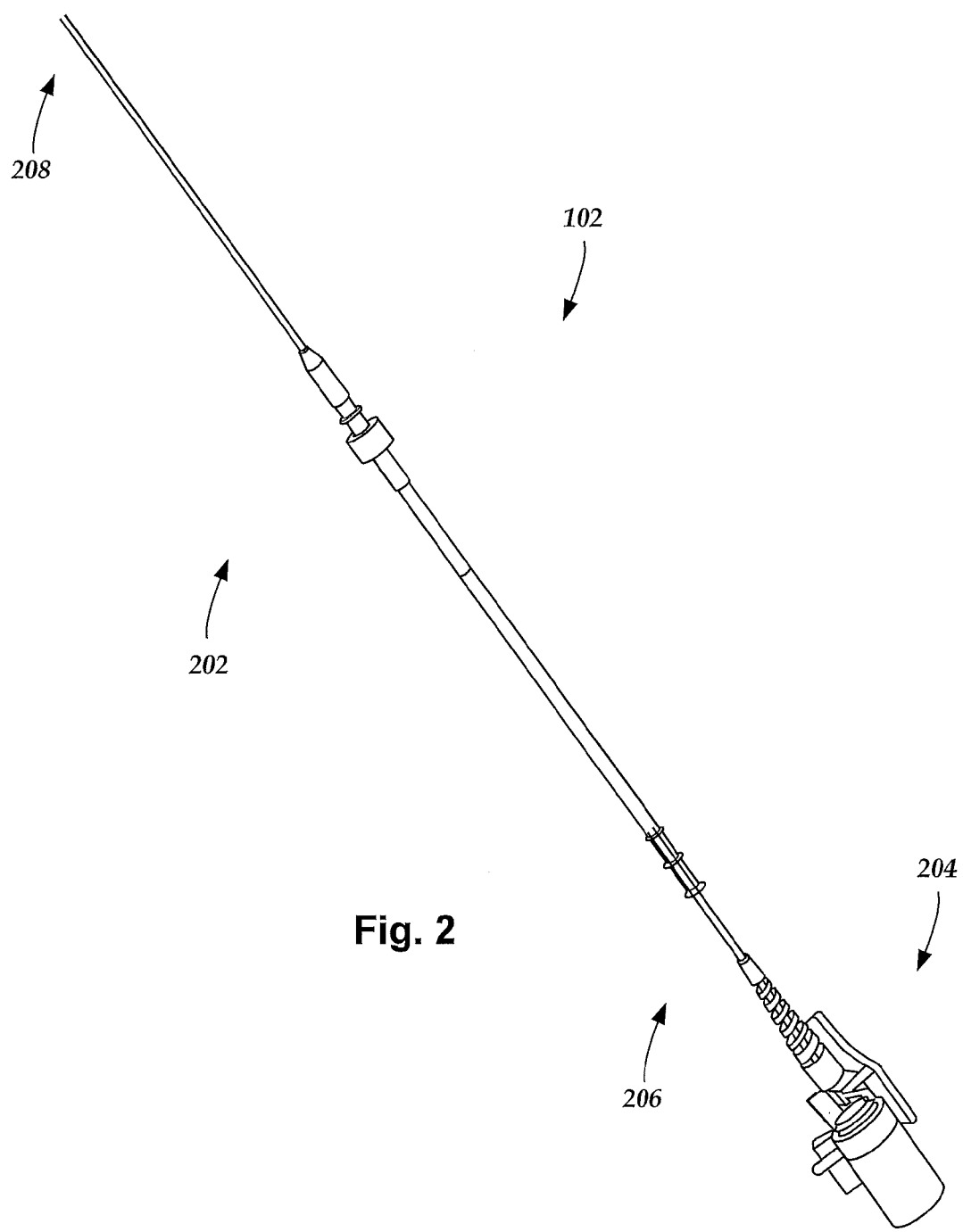
FIG. 2 is a schematic side view of one embodiment of the catheter of FIG. 1, according to the invention.

FIG. 2 is a schematic side view of one embodiment of the catheter 102 of the IVUS imaging system (100 in FIG. 1). The catheter 102 includes an elongated member 202 and a hub 204 (e.g., a connector). The elongated member 202 includes a proximal end 206 and a distal end 208. In FIG. 2, the proximal end 206 of the elongated member 202 is coupled to the catheter hub 204 and the distal end 208 of the elongated member is configured and arranged for percutaneous insertion into a patient. The hub 204 may be configured and arranged to couple to the control module (104 in FIG. 1). In some embodiments, the elongated member 202 and the hub 204 are formed as a unitary body. In other embodiments, the elongated member 202 and the catheter hub 204 are formed separately and subsequently assembled together.

Figure 3:
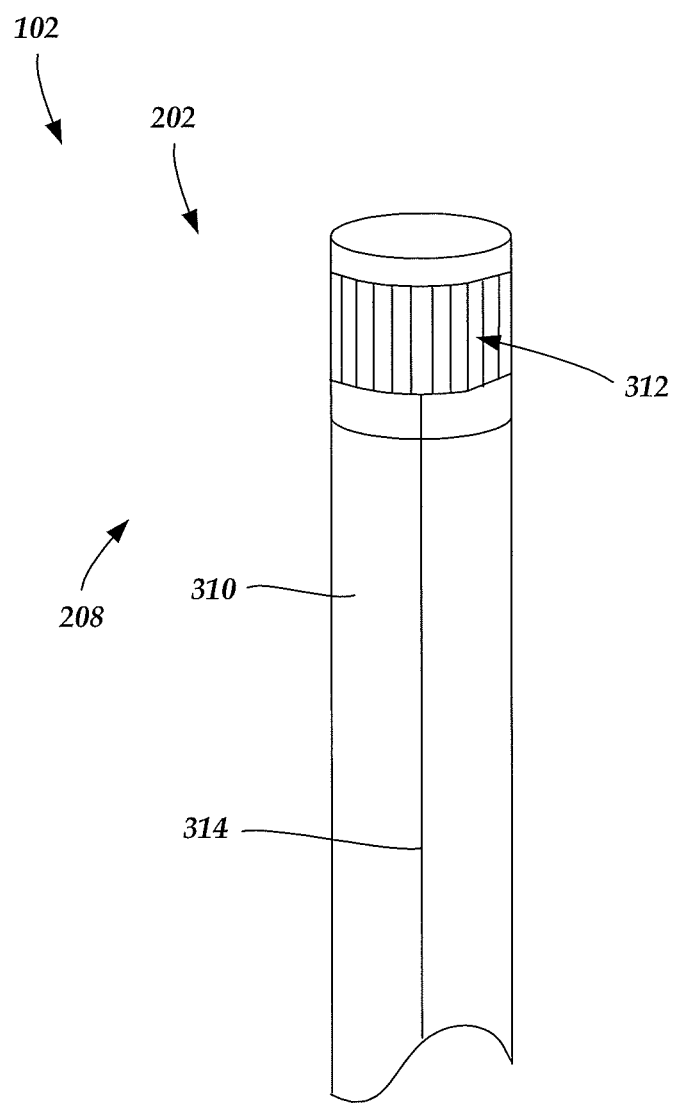
FIG. 3 is a schematic longitudinal cross-sectional view of one embodiment of a distal end of the catheter of FIG. 1 with an imaging core disposed in a lumen defined in a sheath, according to the invention.

FIG. 3 is a schematic perspective view of one embodiment of the distal end 208 of the elongated member 202 of the catheter 102. An array of transducers 312 is disposed at the end of a shaft 310 of the elongated member 202 to transmit and receive acoustic signals. The array of transducers can be provided in any suitable arrangement such as the circumferential array of elongated transducers illustrated in FIG. 3. The transducers 312 may be formed from one or more known materials capable of transforming applied electrical pulses to pressure distortions on the surface of the transducers 312, and vice versa. Examples of suitable materials include piezoelectric ceramic materials, piezocomposite materials, piezoelectric plastics, barium titanates, lead zirconate titanates, lead metaniobates, polyvinylidenefluorides, and the like. Other transducer technologies include composite materials, single-crystal composites, and semiconductor devices (e.g., capacitive micromachined ultrasound transducers ("cMUT"), piezoelectric micromachined ultrasound transducers ("pMUT"), or the like).

The transducers 312 can be used to form a radial cross-sectional image of a surrounding space. Thus, for example, when the transducers 312 are disposed on the catheter 102 and inserted into a blood vessel of a patient, the transducers 312 may be used to form an image of the walls of the blood vessel and tissue surrounding the blood vessel. Because the transducers in the illustrated embodiment are disposed around the entire circumference of the shaft, there is no need for the transducers or shaft to rotate.

The transducers 312 emit acoustic pulses in different radial directions. When an emitted acoustic pulse with sufficient energy encounters one or more medium boundaries, such as one or more tissue boundaries, a portion of the emitted acoustic pulse is reflected back to the emitting transducer as an echo pulse. Each echo pulse that reaches a transducer with sufficient energy to be detected is transformed to an electrical signal in the receiving transducer. The transformed electrical signals are transmitted to the control module (104 in FIG. 1) where the processor 106 processes the electrical-signal characteristics to form a displayable image of the imaged region based, at least in part, on a collection of information from each of the acoustic pulses transmitted and the echo pulses received. The processing of these signals is described in more detail below.

The array of transducers 312 can be provided around the surface of the catheter 102 so that a plurality of images can be formed that collectively form a radial cross-sectional image of a portion of the region surrounding the transducers 312, such as the walls of a blood vessel of interest and the tissue surrounding the blood vessel. The radial cross-sectional image can, optionally, be displayed on one or more displays 112 (FIG. 1).

The array of transducers 312 may move longitudinally along the blood vessel within which the catheter 102 is inserted so that a plurality of cross-sectional images may be formed along a longitudinal length of the blood vessel. In some embodiments, the catheter 102 can include at least one telescoping section that can be retracted or extended during pullback or insertion of the array of transducers 312.

The quality of an image produced at different depths from the transducers 312 may be affected by one or more factors including, for example, bandwidth, transducer focus, beam pattern, as well as the frequency of the acoustic pulse. The frequency of the acoustic pulse output from the transducers 312 may also affect the penetration depth of the acoustic pulse output from the transducers 312. In general, as the frequency of an acoustic pulse is lowered, the depth of the penetration of the acoustic pulse within patient tissue increases. In at least some embodiments, the IVUS imaging system 100 operates within a frequency range of 5 MHz to 100 MHz, for example, at a frequency of at least 20, 25, 30, 40, or 50 MHz.

One or more conductors 314 electrically couple the transducers 312 to the control module 104 (see e.g., FIG. 1). The one or more conductors 314 extend along a longitudinal length of the shaft 310.

The catheter 102 with the array of transducers 312 mounted at the distal end 208 may be inserted percutaneously into a patient via an accessible blood vessel, such as the femoral artery, femoral vein, or jugular vein, at a site remote from the selected portion of the selected region, such as a blood vessel, to be imaged. The catheter 102 may then be advanced through the blood vessels of the patient to the selected imaging site, such as a portion of a selected blood vessel.

Many conventional intravascular ultrasound devices utilize an imaging core with one or more transducers that are rotated to obtain ultrasound signals around the full circumference of the device. Such devices require a rotating motor and driveshaft to rotate the transducer(s) which add expense and more possibility of mechanical failure to the design. Other conventional intravascular ultrasound devices utilize a stationary array of transducers. These transducers are often operated one at time to avoid cross-talk between the transducers.

The present devices do not require rotation of the transducers and permit simultaneous reception of signals at a relatively large number of transducers. Such devices may be smaller in diameter than those with rotating transducers. For example, in at least some embodiments the diameter may be no more than 3, 4, 5, or 6 French (1 French=⅓ mm). Moreover, the devices described herein may not need moving parts and may not require flushing of the catheter.

The present devices may operate at relatively high frequency. For example, the device may operate at a frequency of at least 30, 40, 45, or 50 MHz. The bandwidth may also be relatively large; for example, at least 25%, 30%, 40%, 45%, or 50%.

As illustrated in FIG. 3, the intravascular ultrasound device includes an array of transducers. During operation, a first subset of the transducers is selected to transmit an acoustic signal. This first subset of transducers can be referred to as the transmit aperture. In at least some embodiments, the first subset of transducers transmits an unfocused acoustic signal.

A second subset of the transducers is selected to receive echo signals from surrounding material (e.g., blood vessel) that reflects the acoustic signal. This second subset of transducers can be referred to as the receive aperture.

In at least some embodiments, the number of transducers in the first subset is less than the number of transducers in the second subset. In at least some embodiments, the transducers in the first subset are also in the second subset. In some of these embodiments, the transducers of the first subset are centered, or nearly centered, with respect to the transducers of the second subset.

The transducers in the first subset can be spaced apart from each other (i.e., with one or more intervening transducers that are not part of the first subset), but in at least some embodiments the transducers in the first subset are positioned close together and may be arranged so that each transducer in the first subset is immediately adjacent one (if the transducer is on either end of the first subset) or two other transducers of the first subset.

The transducers in the second subset can be spaced apart from each other (i.e., with one or more intervening transducers that are not part of the second subset), but in at least some embodiments the transducers in the second subset are positioned close together and may be arranged so that each transducer in the second subset is immediately adjacent one (if the transducer is on either end of the second subset) or two other transducers of the second subset.

Each of the transducers of the second subset receives an echo signal. The echo signals from the transducers of the second subset are combined together into a combined signal with each received echo signal multiplied by a selected coefficient. In at least some embodiments, the transmit/receive procedure is repeated at least as many times as there are transducers in the second subset to obtain a set of combined signals. The coefficients are individually selected during each transmit/receive cycle, as described in more detail below, so that the set of combined signals can be further combined by selective addition and subtraction to recover a composite signal for any one of the individual transducers of the second subset. An image of the portion of the surrounding material that reflects the acoustic signal can then be determined from these signals.

Once the procedure has been completed for a specific first subset of transducers, a new first subset of transmitting transducers and a new second subset of receiving transducers can be selected to image a different portion of the surrounding material (e.g., blood vessel). In addition, in some embodiments, the array of transducers can be moved along the object (e.g., a blood vessel) with the imaging procedure performed at each position. The arrangements and methods described herein can result in improved signal-to-noise over devices that transmit/receive at each transducer sequentially.

Figure 4:
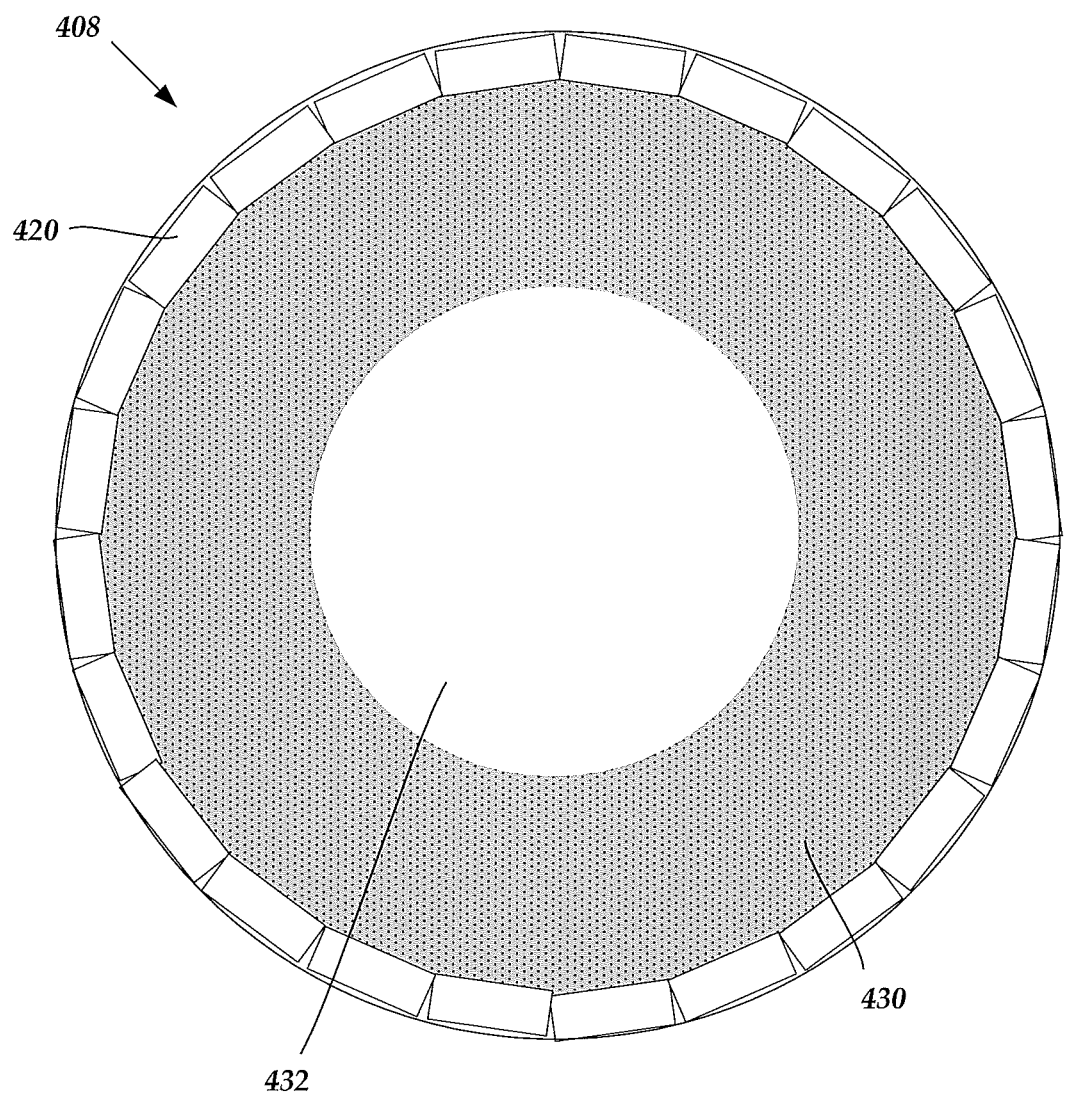
FIG. 4 is a schematic lateral cross-sectional view of one embodiment of an imaging core with a circumferential array of transducer elements, according to the invention.

FIG. 4 is a cross-sectional view of one embodiment of a distal end of a catheter 408 with a circumferential array of transducers 420. In at least some embodiments, each transducer is a CMUT (or any other suitable type) transducer formed on a semiconductor (or other suitable) substrate. The semiconductor substrate may be mounted on a flex circuit or the like and the semiconductor substrate/flex circuit may include other electronic components such as switches or electrodes for operation of the transducers. The flex circuit or semiconductor substrate can include contact sites for attaching the conductors that extend along the catheter to the imaging core.

In some embodiments, such as that illustrated in FIG. 4, the transducers are disposed on a backing material 430 which is preferably acoustically lossy. Any suitable lossy material can be used including, for example, epoxy which may include metal particles, such as titanium particles. In at least some embodiments, the catheter 408 may include a guidewire lumen 432 to accommodate a guidewire to facilitate delivery and positioning of the catheter within the blood vessel or other structure that is to be imaged.

It will be understood that the imaging core can include any number of transducers including, for example, 8, 10, 12, 16, 20, 24, 30, 32, 40, 48, 50, 64, 75, 96, 100, 128, 144, 200, or any other number of transducers. For ease of illustration, the array in FIG. 4 has been illustrated with 24 transducers, but it will be understood that many arrays will have substantially more transducers. It will also be understood that these transducers may be arranged in a one dimensional array, for example, around the circumference of the catheter. It will also be understood that the transducers may be arranged around the entire circumference of the catheter or around only a portion of the circumference. In other embodiments, the catheter may have a non-circular cross-section (e.g., a cross-section in the shape of a square, rectangle, triangle, hexagon, octagon, decagon, dodecagon, oval, or any other regular or irregular shape) with the transducers disposed on one or more surfaces (and in some instances, each surface) of the catheter and preferably around the perimeter, or a portion of the perimeter, of the catheter.

In some embodiments, the transducers may be elongated as illustrated in FIG. 3. As an example, the length (along the longitudinal direction of the catheter) of the transducers may be in the range of 0.1 to 1 mm with a width (around the circumference of the catheter) in the range of 10 to 50 µm. It will be understood that transducers with other lengths, widths, or shapes can also be used.

Figure 5:
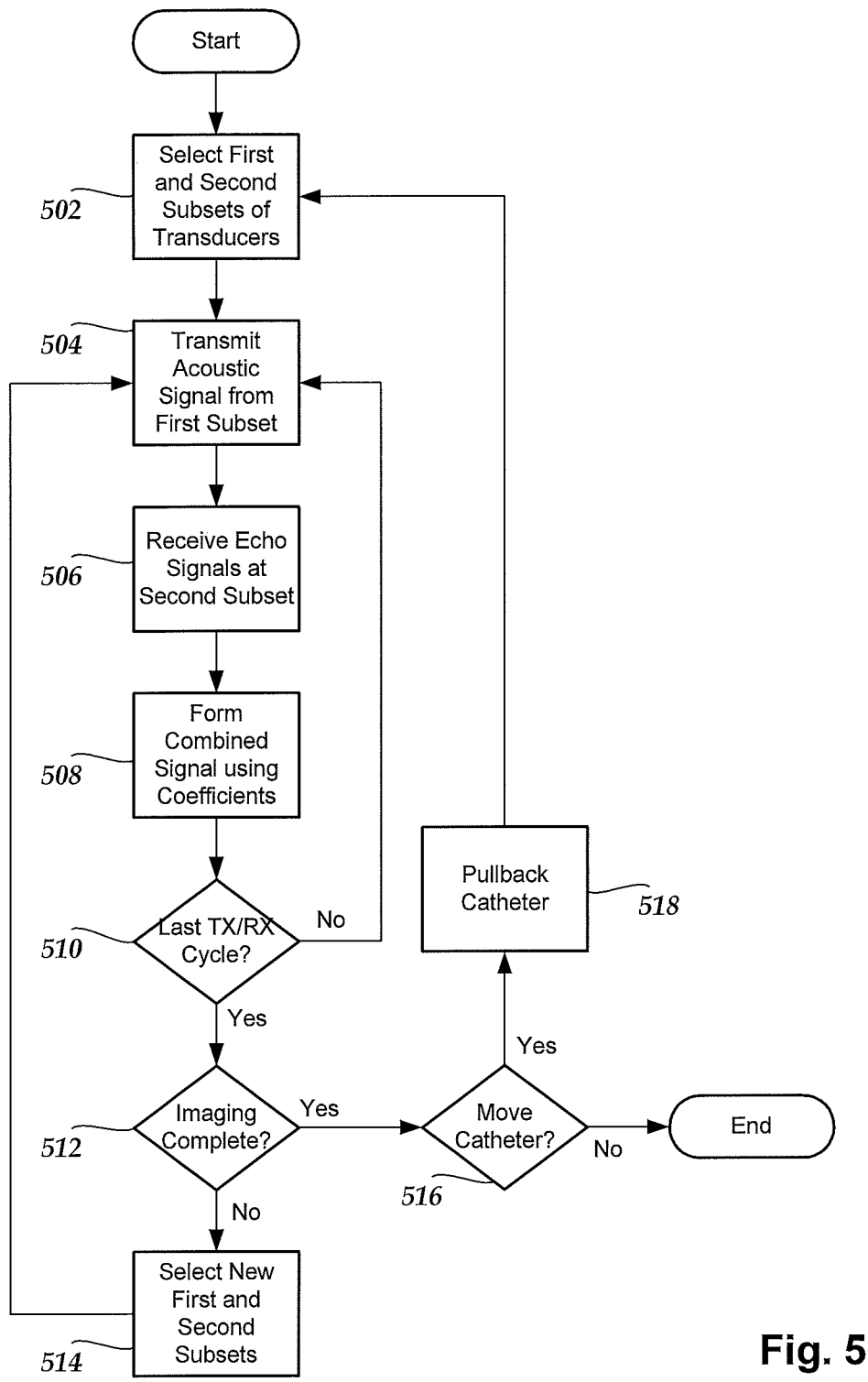
FIG. 5 is a flowchart of one embodiment of a method for obtaining signals from an array of transducers, according to the invention.

One example of a method of obtaining signals using an imaging core with an array of transducers is provided in flowchart form in FIG. 5. A first subset of M transmitting transducers and a second subset of N receiving transducers are selected in step 502, where M, N are integers that are equal to or less than a total number of transducers in the array of transducers and, preferably, N>M. In at least some embodiments, N≥2M or N≥4M or N≥6M or N≥8M. As an example, using an embodiment with 144 transducers, a first subset includes eight neighboring transducers and the second subset includes 48 neighboring transducers including the transducers of the first subset.

In step 504, the transducers of the first subset transmit an acoustic signal. The acoustic signal interacts with the surrounding material (e.g., patient intravascular tissue) and a portion of the acoustic signal is reflected or otherwise redirected back toward the transducers of the second subset. In step 506, the transducers of the second subset each receive an echo signal. In step 508, the received echo signals from the transducers of the second subset are combined to form a combined signal using coefficients that are selected to allow recovery of composite signals (i.e., a combination of signals from multiple transmit/receive cycles (steps 504 and 506)) for each individual transducer. Steps 504-508 are a single transmit/receive (TX/RX) cycle. Steps 504-508 are then repeated until at least N combined signals are obtained (step 510) meaning that the last transmit/receive (TX/RX) cycle has been performed for this selection of first and second subsets. It is these N combined signals that can be further combined by selective addition and subtraction to recover the composite signal for each individual transducer in the second subset.

In at least one embodiment, the combined signal C(h,t) for the h-th transmit/receive cycle over time, t, has the form $$C(h, t) = \sum_{e=1}^{N} H_{he} R(e, t),$$

where R(e,t) is the echo signal from the e-th transducer of the second subset for the h-th transmit/receive cycle, and $H_{he}$ is a non-zero coefficient selected from the matrix H. In at least some embodiments, $H_{he}$ is either +1 or −1. In at least some embodiments, the combination of all of the coefficients $H_{he}$ form a Hadamard matrix. A Hadamard matrix is a square matrix whose entries are either +1 or −1 and whose rows are mutually orthogonal.

Figure 6A:
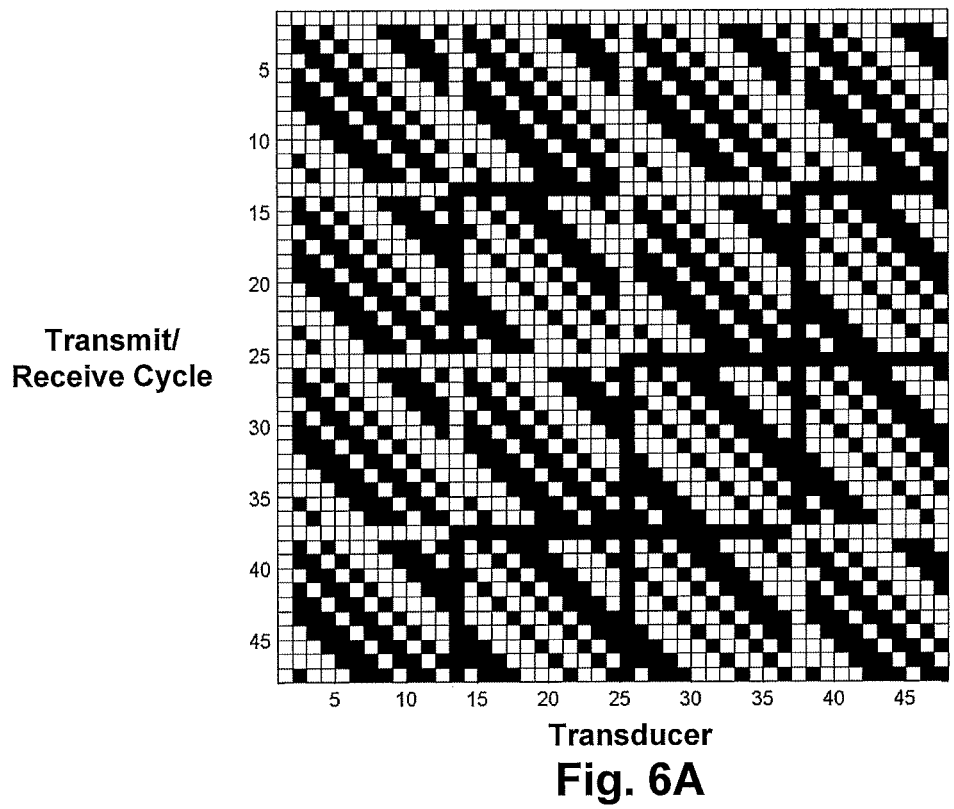
FIGS. 6A and 6B are two embodiments of a matrix identifying coefficients for forty-eight transducers over forty-eight transmit/receive cycles, according to the invention.
Figure 6B:
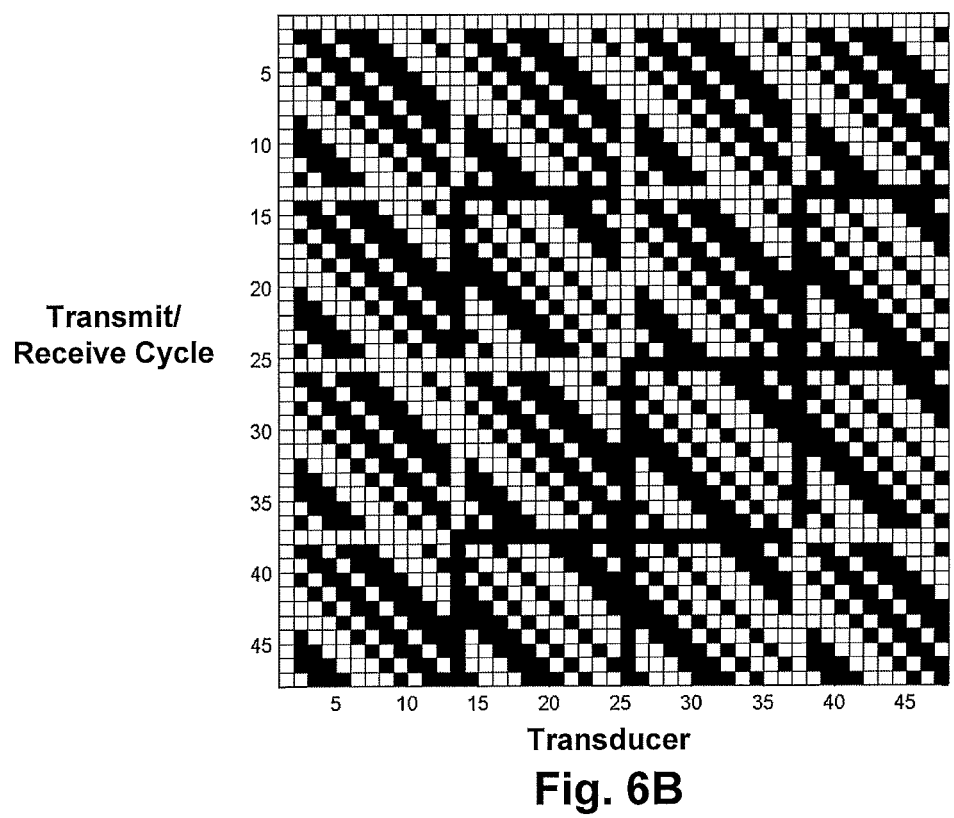

FIGS. 6A and 6B illustrate two different matrices H with different selections of coefficients $H_{he}$ (e-th receive transducer of the second subset along the horizontal axis and h-th transmit/receive cycle along the vertical axis) for 48 transducers and 48 transmit/receive cycles to allow recovery of composite signals for each individual transducer. In FIGS. 6A and 6B, a white square can correspond to a coefficient of +1 and a black square can correspond to a coefficient of −1 (the reverse assignment of +1 and −1 will work equally as well). Each combined signal is generated by adding the individual transducer signals using the coefficients along one row of FIG. 6A or 6B. The selection of coefficients in FIGS. 6A and 6B allow the combination of the 48 different (one for each row in the matrix of FIG. 6A or 6B) combined signals by selective addition and subtraction of those signals to obtain a composite signal for any single one of the receive transducers of the selected second subset, where the composite signal D(e,t) for the e-th transducer is $$D(e, t) = \sum_{h=1}^{N} H_{eh}^T C(h, t) = NR(e, t),$$

where $H_{eh}^T$ is a coefficient obtained from the transpose of the matrix H identified above and C(h,t) is the combined receive signal for the h-th transmit/receive cycle.

In at least some embodiments, the individual transducer composite signals are processed to obtain an ultrasound image. In at least some embodiments, motion compensation can be employed in processing the signals to obtain an ultrasound image, as described in more detail below. In at least some embodiments, each transmit/receive cycle can take, for example, 15-20 microseconds. Thus, the total process for one first subset of transducers, with 48-50 transmit/receive cycles, can be, for example, 1 millisecond or less.

Once all of the transmit/receive cycles have been performed for a selected first subset of transducers and if imaging at the site is not complete (step 512) different first and second subsets of transducers can be selected (step 514) and the transmit/receive cycle process of steps 504-510 performed for the new first and second subsets of transducers. The new first and second subsets of transducers can be selected to, for example, image a different region of material (e.g., a blood vessel) near the array of the transducers.

Any new first and second subsets of transducers can be selected. For example, referring to the arrangement in FIG. 4, the new subsets could be selected by moving clockwise or counterclockwise by one (or two or four or eight or any other number) transducer(s). Any other suitable method for selecting new first and second subsets can also be used. As an example, using the arrangement of FIG. 4, twenty-four different first subsets could be sequentially selected to produce 360° imaging around the circumferential array of transducers illustrated in FIG. 4. In at least some embodiments, the process can be performed at a rate of, for example, 30, 40, 50, or more frames per second, where each frame corresponds to one selected first subset. In at least some embodiments, the imaging resolution is at least 200, 100, or 50 micrometers.

Once all of the desired first and second subsets of transducers have been selected and the transmit/receive cycle process performed at the current position of the imaging core, the array of transducers may be optionally moved (steps 516-518) by, for example, pulling back the catheter (or moving it forward) to a new position and the procedure of steps 502-514 performed at the new position. This can be repeated at any number of new positions of the array of transducers in order to generate ultrasound images at each position which may be viewed separately or combined together for a "three-dimensional" image.

Figure 7:
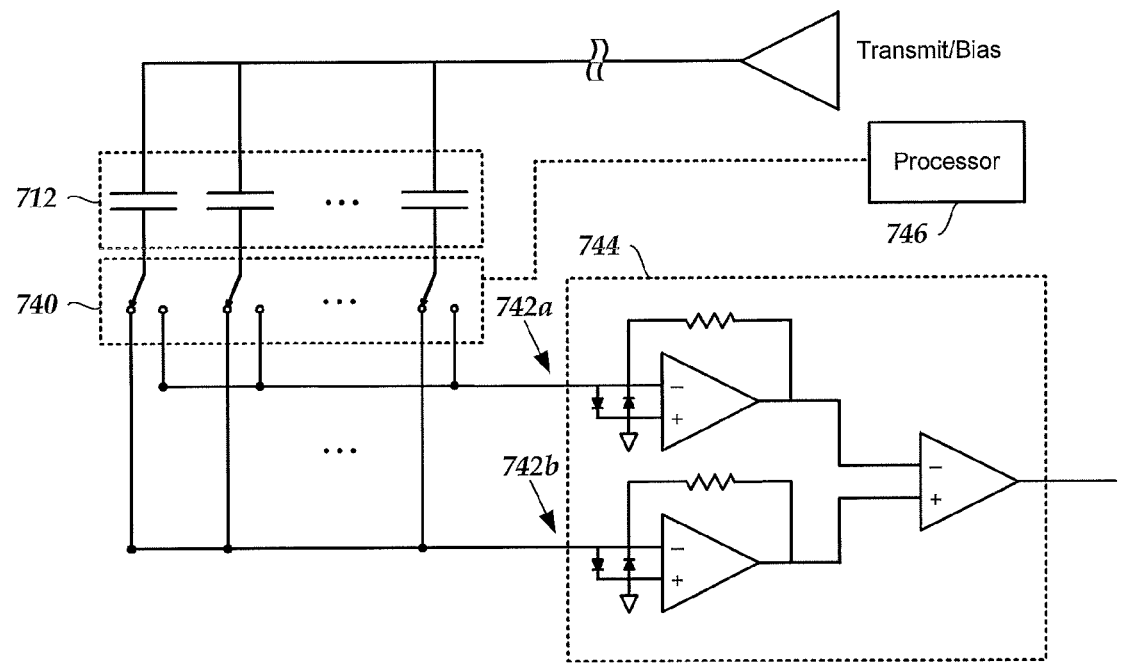
FIG. 7 is a schematic diagram of one embodiment of circuitry for combining echo signals received at an array of transducers, according to the invention.

FIG. 7 is a diagram schematically illustrating one embodiment of circuitry for implementing the combination of echo signals from the transducers using selective coefficients. In FIG. 7, the transducers 712 are coupled to individual switches 740 that determine to which input 742a, 742b of a combiner 744 the echo signal generated by that transducer will be sent. One input corresponds to a positive coefficient and the other input to a negative coefficient. The switches 740 are individually controlled by a processor 746. The switches 740, the combiner 744, the processor 746, or any combination thereof (or combination of components that form these elements) can be incorporated into the same substrate as the transducer elements, on the same flex circuit as the transducer elements, within the same catheter or imaging core as the transducer elements, in the control unit coupled to the catheter, or any combination thereof. Any combination of these components (e.g., the switches 740, the combiner 744, or the processor 746) may be formed as one or more integrated circuits. For example, the switches 740 may be incorporated in the same substrate or on the same flex circuit as the transducer elements and the combiner and processor can be incorporated in the control unit. It will be understood that the processor may also direct operation of additional switches (not shown) that are used to select the first and second subsets of transducers for each transmit/receive cycle.

In at least some embodiments, motion compensation can be provided by including one or more additional transmit/receive cycles to those performed for any give subset of transducer (for example, performing N+1 or N+2 or N+3 transmit/receive cycles instead of N cycles). Any number of additional transmit/receive cycles may be used including one, two, three, four, six, eight, ten, twelve, or more additional cycles.

In some embodiments, the combined signal is generated for these additional one or more transmit/receive cycles utilizing the same coefficients as a previous transmit/receive cycle. For example, a transmit/receive cycle at the end of the series of cycles can produce a combined signal using the same coefficients as used for the first transmit/receive cycle (or any other transmit/receive cycle). Additionally or alternatively, a transmit/receive cycle can be added in the middle of the series of cycles (or at any other position within the series of cycles) to produce a combined signal using the same coefficients as used for the first transmit/receive cycle (or any other transmit/receive cycle). The correlation between these transmit/receive cycles can be determined and used to estimate motion.

In other embodiments, the additional transmit/receive signals for the transducers may be added together or combined in any other fashion. In some embodiments, two or more consequtive transmit/receive cycles may be combined to improve the signal-to-noise ratio. As one example, the receive signals from the receive transducers for three transmit/receive cycles are combined for a motion detection signal. The motion detection signal is obtained at regular time intervals, $\Delta_p$ (for example, every 10, 15, 20, 25, 28, 30, 35, or 40 transmit/receive cycles.) The correlation between these motion detection signals can be determined and used to estimate motion during $\Delta_p$.

As one example, $R_{mc}(e, t)$ is the echo signal from the e-th transducer of the second subset for the motion correction transmit/receive cycle at time t and $R_{mc}(e, t+\Delta_p)$ is the echo signal from the e-th transducer of the second subset for the motion correction transmit/receive cycle at time $t+\Delta_p$. Motion correction can be estimated using the following equation:

$$R_{mc}(e, t + \Delta_p) \approx R_{mc}(e, t) e^{-i4\pi \frac{v_r \Delta_p}{\lambda_0}}$$

where $\lambda_0$ is the transducer center frequency and $v_r$ is the movement velocity. The movement velocity $v_r$ can be estimated by cross-correlation between the received echo signals at times t and t+$\Delta_p$. The movement velocity can then be used to modify the transducer echo signals to account for motion during the transmit/receive cycles. It will be recognized that the motion compensation transmit/receive cycles may use all of the transducers of the first subset for transmission or only some (i.e., one or more) of those transducers. In addition, the motion compensation transmit/receive cycles may use all of the transducers of the second subset to receive corresponding echo signals or only some (i.e., one or more) of those transducers.

Figure 8:
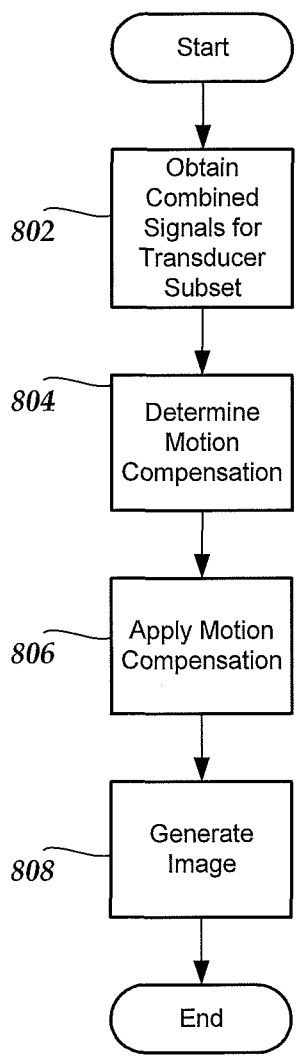
FIG. 8 is a flowchart of one embodiment of a method for processing transducer signals to obtain an image, according to the invention.

FIG. 8 illustrates one method of providing motion compensation. In step 802, the combined signals for the transducer subset are obtained as described above including obtaining combined signals for at least two cycles (for example, the first and last cycles) using the same coefficients. In step 804, motion compensation is determined using the combined signals from the two or more transmit/receive cycles for which the same coefficients were used. The motion compensation can be determined by, for example, determining a correlation between these two or more cycles. In step 806, the motion compensation is then applied to the combined signals or the composite signals for the individual transducers. In step 808, the image is generated using the motion compensated signals.

Because the same coefficients are used to obtain the combined signals, correlation between the combined signals obtained from these two or more transmit/receive cycles can be used to estimate relative motion, particularly axial motion, between the device and the object being imaged. If the signals are highly correlated, then the relative motion is small; generally, the lower the correlation between the signals, the larger the relative motion. The degree of correlation can be used to estimate the motion and to correct the signals determined for each transducer to more accurately assign those signals to corresponding portions of the object being imaged. Using more than one additional transmit/receive cycle for motion correction, assuming that these cycles are spaced apart during the series of cycles, can often provide a finer degree of motion correction.

It will be understood that each block of the flowchart illustrations described above, and combinations of blocks in the flowchart illustrations, as well any portion of the system, methods of obtaining signals using the imaging core, methods of imaging, and any other systems and methods disclosed herein, can be implemented by computer program instructions. These program instructions may be provided to a processor to produce a machine, such that the instructions, which execute on the processor, create means for implementing the actions specified in the flowchart block or blocks or described for the systems and methods disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor. In addition, one or more processes may also be performed concurrently with other processes, or even in a different sequence from that illustrated without departing from the scope or spirit of the invention.

The computer program instructions can be stored on any suitable computer-readable medium (including any non-transitory computer-readable medium) including, but not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computing device.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A medical imaging assembly, comprising:
   an elongated catheter having a proximal end, a distal end, a longitudinal axis, and a connector disposed at the proximal end;
   an array of transducers arranged on the distal end of the catheter, each transducer configured and arranged for transforming applied electrical signals to acoustic signals, transmitting the acoustic signals, receiving corresponding echo signals, and transforming the received echo signals to electrical signals, wherein the array of transducers are arranged circumferentially around an entire circumference of the catheter;
   a plurality of conductors electrically coupled to the array of transducers and in electrical communication with the connector of the catheter; and
   a control unit coupleable to the catheter and configured and arranged to send and receive electrical signals between the control unit and the array of transducers through the connector of the catheter, the control unit comprises a processor configured and arranged to execute instructions, the instructions comprising:
   1) selecting a first subset of M transmitting transducers from the array of transducers and selecting a second subset of N receiving transducers from the array of transducers, wherein M and N are each integers equal to or less than a total number of transducers in the array of transducers and N>M; and
   2) for each of at least N transmit/receive cycles,
      a) directing the first subset of M transmitting transducers to transmit an acoustic signal; and
      b) directing the second subset of N receiving transducers to receive corresponding echo signals arising in response to the transmitted acoustic signal,
   wherein the medical imaging assembly is configured and arranged so that each transducer of the array of transducers can function as i) one of the M transmitting transducers, ii) as one of the N receiving transducers, or iii) as both one of the M transmitting transducers and one of the N receiving transducers.

2. The medical imaging assembly of claim 1, wherein the instructions further comprise performing instructions 1) and 2) for each of a plurality of different second subsets of N transducers, wherein N is less than the total number of transducers in the array of transducers.

3. The medical imaging assembly of claim 1, wherein N≥2M.

4. The medical imaging assembly of claim 1, wherein the instructions further comprise combining the echo signals from the transducers of the second subset to give a combined signal, wherein the combined signal C(h,t) for the h-th transmit/receive cycle over time, t, has a form $$C(h, t) = \sum_{e=1}^{N} H_{he} R(e, t),$$

wherein R(e,t) is the echo signal from the e-th transducer of the second subset for the h-th transmit/receive cycle, and $H_{he}$ is a non-zero coefficient, wherein the coefficients $H_{he}$ are selected so that a composite signals of the received echo signals from N of the transmit/receive cycles for any one of the transducers of the second subset can be recovered by combining N of the combined signals by selective addition and subtraction of the N combined signals.

5. The medical imaging assembly of claim 4, wherein each $H_{he}$ is selected from +1 or −1.

6. The medical imaging assembly of claim 4, wherein the at least N transmit/receive cycles comprises at least N+1 transmit/receive cycles and wherein, for each of at least two transmit/receive cycles of the at least N+1 transmit/receive cycles, the instructions further comprise combining the echo signals for that transmit/receive cycle to give the combined signal using identical coefficients H, for the at least two transmit/receive cycles.

7. The medical imaging assembly of claim 6, wherein the instructions further comprise determining a motion compensation using the combined signals of the at least two transmit/receive cycles generated by combining the echo signals using identical coefficients $H_{he}$ for the at least two transmit/receive cycles.

8. The medical imaging assembly of claim 6, wherein the at least two transmit/receive cycles comprises a first one of the at least N+1 transmit/receive cycles and a last one of the at least N+1 transmit/receive cycles.

9. A medical imaging assembly, comprising:
an elongated catheter having a proximal end, a distal end, a longitudinal axis, and a connector disposed at the proximal end;
an array of transducers arranged on the distal end of the catheter, each transducer configured and arranged for transforming applied electrical signals to acoustic signals, transmitting the acoustic signals, receiving corresponding echo signals, and transforming the received echo signals to electrical signals;
a plurality of conductors electrically coupled to the array of transducers and in electrical communication with the connector of the catheter; and
a control unit coupleable to the catheter and configured and arranged to send and receive electrical signals between the control unit and the array of transducers through the connector of the catheter, the control unit comprises a processor configured and arranged to execute instructions, the instructions comprising:
1) selecting a first subset of M transmitting transducers from the array of transducers and selecting a second subset of N receiving transducers from the array of transducers, wherein M and N are each integers equal to or less than a total number of transducers in the array of transducers and N>M; and
2) for each of at least N transmit/receive cycles,
a) directing the first subset of M transmitting transducers to transmit an acoustic signal; and
b) directing the second subset of N receiving transducers to receive corresponding echo signals arising in response to the transmitted acoustic signal,
wherein the instructions further comprise combining the echo signals from the transducers of the second subset to give a combined signal, wherein the combined signal C(h,t) for the h-th transmit/receive cycle over time, t, has a form $$C(h, t) = \sum_{e=1}^{N} H_{he} R(e, t),$$

wherein R(e,t) is the echo signal from the e-th transducer of the second subset for the h-th transmit/receive cycle, and $H_{he}$ is a non-zero coefficient, wherein the coefficients $H_{he}$ are selected so that a composite signal of the received echo signals from N of the transmit/receive cycles for any one of the transducers of the second subset can be recovered by combining N of the combined signals by selective addition and subtraction of the N combined signals.

10. The medical imaging assembly of claim 9, wherein each $H_{he}$ is selected from +1 or −1.

11. The medical imaging assembly of claim 9, wherein the instructions further comprise generating an ultrasound image using the combined signals.

12. The medical imaging assembly of claim 9, wherein the at least N transmit/receive cycles comprises at least N+1 transmit/receive cycles and wherein, for each of at least two transmit/receive cycles of the at least N+1 transmit/receive cycles, the instructions further comprise combining the echo signals for that transmit/receive cycle to give the combined signal using identical coefficients $H_{he}$ for the at least two transmit/receive cycles.

13. The medical imaging assembly of claim 12, wherein the instructions further comprise determining a motion compensation using the combined signals of the at least two transmit/receive cycles generated by combining the echo signals using identical coefficients $H_{he}$ for the at least two transmit/receive cycles.

14. The medical imaging assembly of claim 12, wherein the at least two transmit/receive cycles comprises a first one of the at least N+1 transmit/receive cycles and a last one of the at least N+1 transmit/receive cycles.

15. A non-transitory computer-readable medium having processor-executable instructions for processing signals from an array of transducers, the processor-executable instructions when installed onto a device enable the device to perform actions, comprising:
1) selecting a first subset of M transmitting transducers from the array of transducers and selecting a second subset of N receiving transducers from the array of transducers, wherein M and N are each integers equal to or less than a total number of transducers in the array of transducers and N>M; and
2) for each of at least N transmit/receive cycles,
a) directing the first subset of M transmitting transducers to transmit an acoustic signal;
b) directing the second subset of N receiving transducers to receive corresponding echo signals arising in response to the transmitted acoustic signal; and
c) combining the echo signals from the transducers of the second subset to give a combined signal, wherein the combined signal C(h,t) for the h-th transmit/receive cycle over time, t, has a form $$C(h, t) = \sum_{e=1}^{N} H_{he} R(e, t),$$

wherein R(e,t) is the echo signal from the e-th transducer of the second subset for the h-th transmit/receive cycle, and $H_{he}$ is a non-zero coefficient, wherein the coefficients $H_{he}$ are selected so that a composite signals of the received echo signals from N of the transmit/receive cycles for any one of the transducers of the second subset can be recovered by combining N of the combined signals by selective addition and subtraction of the N combined signals.

16. The non-transitory computer-readable medium of claim 15, wherein the instructions further comprise generating an ultrasound image using the combined signals.

17. The non-transitory computer-readable medium of claim 15, wherein the at least N transmit/receive cycles comprises at least N+1 transmit/receive cycles and wherein, for each of at least two transmit/receive cycles of the at least N+1 transmit/receive cycles, the instructions further comprise combining the echo signals for that transmit/receive cycle to give the combined signal using identical coefficients $H_{he}$ for the at least two transmit/receive cycles.

18. The non-transitory computer-readable medium of claim 17, wherein the instructions further comprise determining a motion compensation using the combined signals of the at least two transmit/receive cycles generated by combining the echo signals using identical coefficients $c_{ij}$ between the at least two transmit/receive cycles.

19. The non-transitory computer-readable medium of claim 17, wherein the instructions further comprise performing instructions 1) and 2) for each of a plurality of different subsets of N transducers, wherein N is less than the total number of transducers in the array of transducers.

* * * * *